United States Patent [19]

Hirai et al.

[11] Patent Number: 4,663,478

[45] Date of Patent: May 5, 1987

[54] PROCESS FOR PRODUCING A PARA-SUBSTITUTED PHENOL DERIVATIVE

[75] Inventors: Hidefuni Hirai, 14-10, Yutenji 1-chome, Meguro-ku, Tokyo; Makoto Komiyama; Izuru Sugiura, both of Tokyo, all of Japan

[73] Assignee: Hidefuni Hirai, Tokyo

[21] Appl. No.: 725,360

[22] PCT Filed: Feb. 13, 1985

[86] PCT No.: PCT/JP85/00057

§ 371 Date: Apr. 18, 1985

§ 102(e) Date: Apr. 18, 1985

[87] PCT Pub. No.: WO85/03701

PCT Pub. Date: Aug. 29, 1985

[30] Foreign Application Priority Data

Feb. 14, 1984 [JP] Japan ................................. 59-25589
Apr. 12, 1984 [JP] Japan ................................. 59-73300
Apr. 19, 1984 [JP] Japan ................................. 59-79067

[51] Int. Cl.$^4$ ............................................. C07C 65/04
[52] U.S. Cl. ................................. 562/475; 562/508; 568/377; 568/657; 568/813
[58] Field of Search ............... 562/475, 508; 568/377, 568/657, 813

[56] References Cited

U.S. PATENT DOCUMENTS 4,523,031 6/1985 Hirai et al. ......................... 562/475

FOREIGN PATENT DOCUMENTS 0073837 3/1983 European Pat. Off. .
170729 10/1983 Japan .
194835 11/1983 Japan .

OTHER PUBLICATIONS

JACS, vol. 105, No. 7, 2018–2021 (1983).
JACS, vol. 106, No. 1, 174–178 (1984).
Tetrahedron Letters, No. 20, 1645–1646 (1976).

*Primary Examiner*—Paul J. Killos
*Attorney, Agent, or Firm*—Sprung Horn Kramer & Woods

[57] ABSTRACT

By reacting a phenol compound with an organic halide selected from the group consisting of a haloform, a carbon tetrahalide and a substituted or unsubstituted allyl halide in the presence of an alkali metal hydroxide, using as a catalyst a fixed cyclodextrin having hydroxyl groups crosslinked with a bivalent hydrocarbon group having free valences at its both ends, said hydrocarbon group having at least one hydrogen atom substituted or unsubstituted with a member selected from the group consisting of an alkyl group, a halogen atom and a hydroxyl group and containing or not containing at least one combination of two neighboring carbon atoms having therebetween at least one member selected from the group consisting of an oxygen atom, a sulfur atom and a phenylene, various useful para-substituted phenol derivatives can be advantageously obtained. The fixed cyclodextrin which has been used as the catalyst can be extremely easily separated from the reaction system without any loss of the fixed cyclodextrin, and the recovered fixed cyclodextrin can be used repeatedly as a catalyst in the process of the present invention without lowering in yield of and selectivity for para-substituted phenol derivatives.

26 Claims, No Drawings

PROCESS FOR PRODUCING A PARA-SUBSTITUTED PHENOL DERIVATIVE

FIELD OF THE INVENTION

This invention relates to a process for producing a para-substituted phenol derivative. More particularly, the present invention is concerned with a process for producing a para-substituted phenol derivative which comprises reacting a phenol compound with an organic halide selected from the group consisting of a haloform, a carbon tetrahalide and a substituted or unsubstituted allyl halide in the presence of an alkali metal hydroxide, using as a catalyst a fixed cyclodextrin having hydroxyl groups crosslinked with a bivalent hydrocarbon group having free valences at its both ends.

DESCRIPTION OF THE PRIOR ART

It is known that 2,5-cyclohexadienone derivatives having a dihalomethyl group at the 4-position, 2,5-cyclohexadienone derivatives having a substituted or unsubstituted allyl group at the 4-position, para-hydroxybenzoic acid derivatives, or para-hydroxybenzaldehyde derivatives are prepared by reacting a phenol with a haloform under alkaline conditions. The products thus obtained are extremely valuable compounds as pharmaceuticals, agricultural chemicals, or raw materials for polymers, various physiologically active substances such as agricultural chemicals and pharmaceuticals, and dyes.

However, known reaction processes have serious disadvantages or extremely low selectivity and therefore poor yield. Accordingly, the known processes cannot be advantageously used in practice.

For example, para-hydroxybenzaldehyde which, nowadays, is of increasing importance as an anticarcinogen or a raw material for pharmaceuticals, agricultural chemicals and dyes, has conventionally been synthesized by reacting phenol with chloroform in the presence of an alkali. In the reaction, however, para-hydroxybenzaldehyde is obtained in a selectivity as low as about 30%, and a large amount of salicylaldehyde is formed as a by-product. Therefore, the production of para-hydroxybenzaldehyde in accordance with this process requires not only a large amount of raw materials but also a complicated operation for separation.

2,4-Dihydroxybenzaldehyde, nowadays, is also of increasing importance in view of its interesting behaviors such as cancer-controlling effect, plant root growth-promoting effect, antibacterial effect and photophosphorylation-controlling effect in chloroplast. For the production of 2,4-dihydroxybenzaldehyde, known is a process in which 1,3-dihydroxybenzene is reacted with chloroform in the presence of an alkali. However, in this known process, a large amount of 2,4-dihydroxy-3-formylbenzaldehyde is formed as a by-product, and 2,4-dihydroxybenzaldehyde which is the intended product is obtained only in low yield and with low selectivity. Accordingly, for producing 2,4-dihydroxybenzaldehyde by this process, not only large amounts of raw materials but also a complicated operation for separation is required.

As to the production of para-hydroxybenzoic acid which, nowadays, is of increasing importance as a raw material for heat resistant polymers, agricultural chemicals and pharmaceuticals, known is the Kolbe-Schmitt reaction in which para-hydroxybenzoic acid is synthesized by treating phenol with potassium hydroxide and potassium carbonate, followed by heating together with carbon dioxide under pressure. The reaction, however, has disadvantages that a costly pressure resistant apparatus is required because of high pressure applied during the reaction, and that much energy is required for the achievement a highly anhydrous condition which is indispensable to the reaction. Also known is another process in which phenol is reacted with carbon tetrachloride in the presence of an alkali to prepare para-hydroxybenzoic acid. In the process, however, the selectivity for the formation of para-hydroxybenzoic acid is 57%, and the reaction gives a large amount of salicylic acid as a by-product. Therefore, the process also requires not only large amounts of raw materials but also a complicated operation for separation.

2,5-Cyclohexadienone derivatives having an allyl group at the 4-position are also highly reactive due to the conjugation of two C—C double bonds and a carbonyl group, and therefore, are valuable as raw materials for the syntheses of physiologically active substances and other useful substances. Moreover, many of 2,5-cyclohexadienone derivatives themselves have physiological activities. Hitherto is known the Reimer-Tiemann reaction in which a para-substituted phenol is reacted with a haloform and sodium hydroxide or potassium hydroxide to give a 4-dihalomethyl-2,5-cyclohexadienone derivative. The reaction, however, gives as major product a compound having a substituent introduced mainly to the ortho-position. Therefore, the conventional process gives 2,5-cyclohexadienone derivatives in a yield as low as 5 to 10%, and requires not only large amounts of raw materials but also a complicated operation for separation.

2,5-Cyclohexadienone derivatives having an allyl group at the 4-position are also highly reactive due to the conjugation of two C—C double bonds and a carbonyl group. In addition, they have an allyl group at such a position that an intramolecular ring-forming reaction is readily caused to occur. Accordingly, the derivatives are valuable compounds as starting materials for preparing physiologically active substances and other useful substances. 2,5-Cyclohexadienone derivatives having an allyl group at the 4-position have conventionally been prepared by a process comprising two steps, namely, the first step in which a 1:1 mixture of sodium methoxide and a para-substituted phenol is reacted with an allyl halide in an aromatic solvent to produce a 2,4-cyclohexadienone derivative which is allyl-substituted at the 6-position, and the second step in which the product in the first step is then reacted in a methanol-hydrochloric acid mixture to allow the allyl group to transfer to the 4-position. The process, however, has disadvantages that the 2,4-cyclohexadienone derivative which is a reaction product of the first step is difficult to separate and purify, and that the reactions involved in the process require large amounts of organic solvents.

The present inventors have previously found that, when a phenol compound is reacted with an organic halide in the presence of cyclodextrin under an alkaline condition, a substituent group derived from said organic halide is introduced to the 4-position of the phenol compound with high selectivity, and, therefore, the intended para-substituted phenol derivative can be obtained in high yield (European Patent Application Laid-Open Specification No. 0073837). However, as well known, cyclodextrin is soluble in an alkaline aqueous solution, and therefore, for recovering the cyclodextrin after completion of the reaction, it is required to acidify the reaction system by adding an acid thereto to deposite and separate the cyclodextrin therefrom. Such an operation for recovering the cyclodextrin is not only troublesome but also has a disadvantage that 10 to 20% of the cyclodextrin employed for the reaction is usually lost during the step of recovery. Accordingly, since cyclodextrin is highly expensive, the process is extremely disadvantageous in manufacturing the above-mentioned various valuable substances and intermediates thereof by reacting phenols with organic halides on a commercial scale.

On the other hand, hydroxychalcone and its derivatives, nowaday, are of increasing importance as a remedy for gastrointestinal ulcers and tumors, as an anti-inflammatory agent, and as an intermediate for preparing a variety of pharmaceuticals, and agricultural chemicals.

It is already known that 4-hydroxychalcone and its derivatives are prepared by reacting phenol with a haloform in the presence of an alkali to give 4-hydroxybenzaldehyde and reacting the obtained 4-hydroxybenzaldehyde with acetophenone or its derivative. It is also known that 4-hydroxy-3-carboxychalcone derivatives are prepared by reacting 4-hydroxybenzaldhyde with a carbon tetrahalide in the presence of an alkali to give 2-hydroxy-5-formylbenzoic acid and then reacting the obtained 2-hydroxy-5-formylbenzoic acid with acetophenone and its derivatives. However, when the above-mentioned processes are practiced, not only the intended products are obtained only in low yields but also large amounts of by-products are unfavorably produced. Therefore, the above-mentioned processes are impractical.

As described above, any of the conventional processes for preparing para-substituted phenol derivatives are unsatisfactory from a practical point of view because of extremely low selectivity, necessity of complicated steps for recovering the catalyst employed and much loss of catalyst. The elimination of the disadvantages accompanying conventional processes has been strongly desired.

DISCLOSURE OF THE PRESENT INVENTION

The present inventors have made extensive and intensive studies to develop a process for preparing para-substituted phenol derivatives, in which not only para-substituted phenol derivatives can be obtained in high yield and with high selectivity but also the catalyst is not lost and can be recovered easily from the reaction mixture. As a result, the present inventors have surprisingly found that the disadvantages of the conventional processes can be eliminated by using as a catalyst a fixed cyclodextrin having hydroxyl groups crosslinked with a bivalent hydrocarbon group having free valences at its both ends and that the para-substituted phenol derivatives can be prepared extremely advantageously from a practical point of view. Specifically, the present inventors have found that, by employing the above-mentioned fixed cyclodextrin as a catalyst, the intended para-substituted phenol derivatives can be prepared in high yield and with high selectivity (of which the definition will be given later) and that since the fixed cyclodextrin is insoluble in the reaction system the employed fixed cyclodextrin can be recovered with great ease from the reaction mixture, for example, by centrifugation and filtration. Further, it has been surprisingly found that even when the recovered fixed cyclodextrin is repeatedly employed as a catalyst the para-substituted phenol derivatives can be prepared without lowering in yield and selectivity. Based on such novel findings, the present invention has been made.

According to the present invention, there is provided a process for producing a para-substituted phenol derivative which comprises (1) reacting a phenol compound represented by the formula (I)

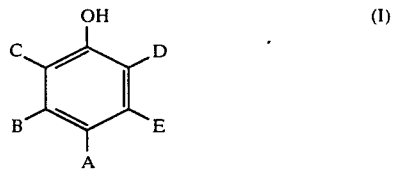

wherein A, B, C, D and E each independently stand for hydrogen, a hydroxyl group, a carboxyl group, a sulfonic group, a halogen atom, a substituted or unsubstituted alkyl group, a substituted or unsubstituted allyl group, a substituted or unsubstituted alkoxyl group or a substituted or unsubstituted aryl group, provided that A does not stand for a hydroxyl group, a carboxyl group and a sulfonic group and that when two or more of A, B, C, D, and E each independently stand for a substituted or unsubstituted alkyl group or a substituted or unsubstituted alkoxyl gruoup, they have their respective free terminal ends or at least one of them is bonded to another group selected from said alkyl and alkoxyl groups to form a ring, with an organic halide selected from the group consisting of a haloform, a carbon tetrahalide and a substituted or unsubstituted allyl halide in the presence of an alkali metal hydroxide, using as a catalyst a fixed cyclodextrin having hydroxyl groups crosslinked with a bivalent hydrocarbon group having free valences at its both ends, said hydrocarbon group having at least one hydrogen atom substituted or unsubstituted with a member selected from the group consisting of an alkyl group, a halogen atom and a hydroxyl group and containing or not containing at least one combination of two neighboring carbon atoms having therebetween at least one member selected from the group consisting of an oxygen atom, a sulfur atom and phenylene, thereby to obtain a reaction mixture containing a para-substituted phenol derivative; and (2) isolating the para-substituted phenol derivative from said reaction mixture.

By the term "phenol compound" as used herein is meant phenol (hydroxybenzene) or its derivative which is defined by the above-mentioned formula (I). The substituted or unsubstituted alkyl group, the substituted or unsubstituted allyl group, the substituted or unsubstituted alkoxyl group and the substituted or unsubstituted aryl group each may preferably have carbon atoms of not more than 6 with respect to the substituents B, C, D and E, and each may preferably have carbon atoms of not more than 12 with respect to the substituent A.

The organic halide which is one of the reactants to be used in the process of the present invention is selected from the group consisting of a haloform, a carbon tetrahalide and a substituted or unsubstituted allyl halide. The substituted or unsubstituted allyl halide may preferably have carbon atoms of not more than 12. As such an allyl halide, the chloride and bromide are especially preferred. The organic halide may be used in an amount of 1 to 20 mols, preferably 1.5 to 10 mols per mol of the phenol compound used.

The alkali metal hydroxide to be used in the process of the present invention may preferably be sodium hydroxide or potassium hydroxide. The alkali metal hydroxide may be used in a stoichiometrical amount relative to the phenol compound. Usually, however, 1 to 15 times, preferably 1.5 to 10 times the stoichiometrical amount of the alkali metal hydroxide may be used taking into consideration of the rate of reaction and the like.

The reaction according to the process of the present invention is usually carried out in a reaction medium. As the reaction medium, there is employed an aqueous solvent, preferably water, because of the requirement that the reaction medium be capable of dissolving the alkali metal hydroxide therein. There may also be used, as the reaction medium, a mixture of water with a small amount of an organic solvent which is soluble in water and can be present stably under the reaction conditions. Examples of such an organic solvent include methanol, ethanol, acetone, dimethoxyethane and the like. The concentration of the alkali metal hydroxide in the reaction solvent may be in the range of 0.1 to 50% by weight. The preferred concentration of the alkali metal halide in the reaction medium varies depending on the kind of the organic halide to be employed. Specifically, where the organic halide is a haloform, the range of concentration is preferably 5 to 20% by weight, more preferably 10 to 15% by weight. Where the organic halide is a carbon tetrahalide or an allyl halide, the range of concentration is preferably 0.1 to 30% by weight, more preferably 0.5 to 25 % by weight. When acetophenone or its derivative is added to the reaction mixture obtained by the reaction of organic halide with a phenol compound to give a hydroxychalcone compound, the concentration of the alkali metal hydroxide in the reaction medium is preferably 5 to 20% by weight.

The fixed cyclodextrin to be used in the process of the present invention is a granular solid or a gel, and the cyclodextrin has hydroxyl groups crosslinked with a bivalent hydrocarbon group having free valences at its both ends. The fixed cyclodextrin is insoluble in the reaction system and remains unchanged chemically during the reaction. The hydrocarbon group may have at least one hydrogen atom substituted with a member selected from the group consisting of an alkyl group, a halogen atom such as fluorine and chlorine, and a hydroxyl group. In this case, an alkyl group having 6 or less carbon atoms is preferred. As the preferable number of substituents, there may be mentioned 4 or less in the case of an alkyl group, 20 or less in the case of a halogen atom, and 10 or less in the case of a hydroxyl group. Moreover, the hydrocarbon group may contain at least one combination of two neighboring carbon atoms having therebetween at least one member selected from the group consisting of an oxygen atom, a sulfur atom and a phenylene. In this case, the number of oxygen atoms, sulfur atoms and phenylenes contained in the hydrocarbon group are preferably 8 or less, 8 or less and 2 or less, respectively. In general, the hydrocarbon group contains preferably 2 to 20 carbon atoms, more preferably 2 to 10 carbon atoms.

As specific examples of the hydrocarbon group, there may be mentioned groups represented by the following general formulae. But the hydrocarbon group is not limited to the groups represented by the following general formulae.

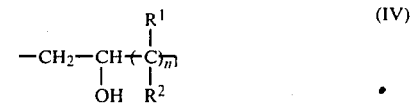

wherein $n^1$ is an integer from 1 to 10, and $R^1$ and $R^2$ each independently stand for a hydrogen atom, a halogen atom, a hydroxyl group or an alkyl group having 6 or less carbon atoms;

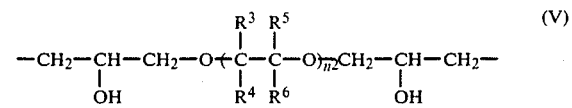

wherein $n^2$ is an integer from 1 to 6, and $R^3$, $R^4$, $R^5$ and $R^6$ each independently stand for a hydrogen atom, a halogen atom, a hydroxyl group or an alkyl group having 6 or less carbon atoms;

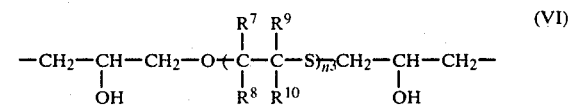

wherein $n^3$ is an integer from 1 to 6, and $R^7$, $R^8$, $R^9$ and $R^{10}$ each independently stand for a hydrogen atom, a halogen atom, a hydroxyl group or an alkyl group having 6 or less carbon atoms; and

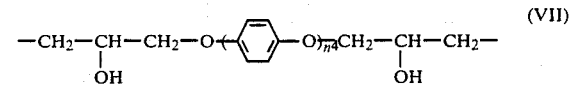

wherein $n^4$ is an integer from 1 to 2. The preferable numbers of halogen atoms, hydroxyl groups and alkyl groups contained in the hydrocarbon group represented by the formulae given above are 20 or less, 10 or less and 4 or less, respectively.

As preferable examples of the hydrocarbon group there may be mentioned 2-hydroxypropylene 2-hydroxybutylene, 2-hydroxypentylene, 2,9-dihydroxy-4,7-dioxadecylene, 2,10-dihydroxy-4,8-dioxaundecylene, and 2,11-dihydroxy-4,9-dioxadodecylene. Of them, 2-hydroxypropylene and 2,9-dihydroxy-4,7-dioxadecylene are more preferred.

As the cyclodextrin to be crosslinked with the bivalent hydrocarbon group having free valences at its both ends, there may be mentioned a modified or unmodified α-, β- or γ-cyclodextrin. A preferable kind of cyclodextrin varies according to the kind of the organic halide to be used.

Specifically, where the organic halide is a haloform, α-cyclodextrin and β-cyclodextrin are preferred, and β-cyclodextrin is more preferred. Where the organic halide is a carbon tetrahalide, β-cyclodextrin is preferred. Where the organic halide is an allyl halide, α-cyclodextrin and β-cyclodextrin are preferred, and α-cyclodextrin is more preferred. When a modified cyclodextrin is used as the cyclodextrin, there may be employed a modified α-, β- or γ-cyclodextrin of which the primary hydroxyl groups are all or partly substituted, for example, with a methoxy group. When an allyl halide is used as the organic halide, a fixed modified α-cyclodextrin is particularly preferred. Incidentally, the modified cyclodextrin may be prepared according to the method described in Helv. Chim. Acta, 61, 2190 (1978).

The fixed cyclodextrin in which a modified or unmodified cyclodextrin has hydroxyl groups crosslinked can be obtained by reacting the cyclodextrin with a crosslinking agent in the presence of an alkali metal hydroxide such as potassium hydroxide and sodium hydroxide. As the crosslinking agent, there may be employed crosslinking agents represented by the formulae (IV'), (V'), (VI') and (VII') which respectively correspond to the hydrocarbon groups represented by the above-described formulae (IV), (V), (VI) and (VII).

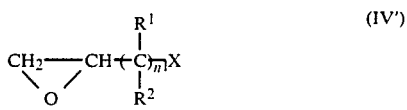

wherein X stands for a halogen atom, preferably a chlorine atom or a bromine atom, and $n^1$, $R^1$ and $R^2$ are as defined above;

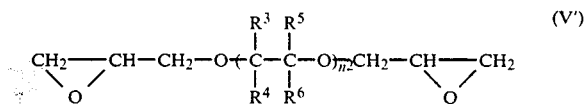

wherein $n^2$, $R^3$, $R^4$, $R^5$ and $R^6$ are as defined above;

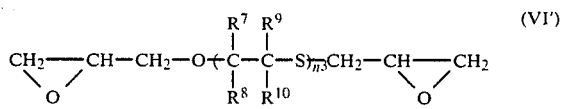

wherein $n^3$, $R^7$, $R^8$, $R^9$ and $R^{10}$ are as defined above; and

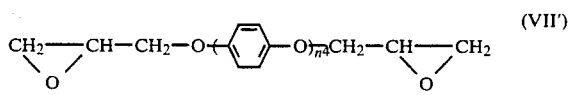

wherein $n^4$ is as defined above.

In view of availability and ease in handling and catalytic performance of the resulting fixed cyclodextrin, epichlorohydrin, epibromohydrin and ethylene glycol diglycydyl ether are preferably employed as the crosslinking agent.

The molar ratio of the crosslinking agent to cyclodextrin in the reaction for crosslinking is preferably 1.0 to 30, and the molar ratio of the alkali metal hydroxide to the crosslinking agent is preferably in the range of 1.0 to 2.0. The crosslinking reaction can be carried out in the presence of both of an alkali metal hydroxide and sodium borohydride. In this case, the molar ratio of sodium borohydride to the crosslinking agent is preferably in the range of 0.001 to 0.1. The reaction is generally effected at a temperature of 40° to 90° C. The reaction time is not critical, but is generally 10 minutes to 4 hours.

The cyclodextrin content of the fixed cyclodextrin employed in the process of the present invention is preferably in the range of 20 to 96% by weight, more preferably in the range of 40 to 96%. The cyclodextrin content of the fixed cyclodextrin can easily be adjusted by varying the kind of the crosslinking agent, the molar ratio of the crosslinking agent to cyclodextrin or the like. When the fixed cyclodextrin is granular solid, the cyclodextrin content may be determined by means of elementary analysis. When the fixed cyclodextrin is a gel, the cyclodextrin content may be determined by means of $^1$H-NMR.

In the process of the present invention, the molar ratio of the fixed cyclodextrin on the basis of cyclodextrin in the fixed cyclodextrin (hereinafter often referred to simply as "fixed cyclodextrin") to the organic halide is preferably 0.001 to 20. A more preferable range of the ratio of the fixed cyclodextrin to the organic halide varies depending on the kind of the organic halide to be used. Specifically, where the organic halide is a haloform, the molar ratio of the fixed cyclodextrin to the organic halide is preferably 0.5 to 10, more preferably 0.8 to 5. Where the organic halide is a carbon tetrahalide, the molar ratio of the fixed cyclodextrin to the carbon tetrahalide is preferably 0.001 to 5. Where the organic halide is an allyl halide, the molar ratio of the fixed cyclodextrin to the allyl halide is preferably 0.01 to 10, more preferably 0.1 to 5.

In practicing the process of the present invention, all the amount of the organic halide to be used may be added to a solution containing a phenol compound, an alkali metal hydroxide and a fixed cyclodextrin at the time of initiation of the reaction. Alternatively, the organic halide may be added to a system comprising a phenol compound, an alkali metal hydroxide and a fixed cyclodextrin so that the molar ratio of the fixed cyclodextrin to the organic halide is maintained at a value falling within the range as mentioned above. The latter mode of process can be practiced by intermittently or gradually adding the organic halide to the above-mentioned system. In this mode of process, the para-substituted phenol derivatives can be obtained at a high selectivity even by the use of a small amount of the fixed cyclodextrin, leading to economical advantages. In this case, the control of the molar ratio of the fixed cyclodextrin to the organic halide in the reaction system may be made by the following method. During the course of the reaction, at predetermined time intervals, part of the reaction mixture is taken, subjected to the determination of the organic halide contained therein by gas chromatography, and the rate of addition of the organic halide to the reaction system is adjusted so that the molar ratio of the fixed cyclodextrin to the organic halide is maintained at a value falling within the range as mentioned above.

In the process of the present invention, in general, the fixed cyclodextrin may be used in an amount of 0.00001 to 10 in terms of molar ratio with respect to the phenol compound used. A preferable molar ratio of the cyclodextrin to the phenol compound varies depending on the kind of the organic halide to be used. Specifically, where the organic halide is a haloform, the molar ratio of the fixed cyclodextrin to the phenol compound is preferably 0.00001 to 5, more preferably 0.01 to 5, particularly preferably 0.5 to 5. Where the organic halide is a carbon tetrahalide, the molar ratio of the cyclodextrin to the phenol compound is preferably 0.001 to 10, more preferably 0.001 to 1, particularly preferably 0.01 to 0.5. Where the organic halide is an allyl halide, the molar ratio of the fixed cyclodextrin to the allyl halide is preferably 0.0001 to 10, more preferably 0.01 to 10, particularly preferably 0.1 to 5.

The reaction temperature is not critical, and may be suitably determined according to a phenol compound to be used, but generally is 0° to 120° C., preferably 20° to 100° C.

The reaction time is also not critical, and may be suitably determined according to the kinds of a phenol compound and an organic halide to be used, the amounts of reactants, reaction temperature, manner of addition of reactants and the like but generally is 10 minutes to 40 hours.

The reaction pressure is also not restricted, and the reaction is usually carried out at atmospheric pressure from a viewpoint of ease in operation.

By the reaction of the phenol compound with the organic halide according to the process of the present invention, there is produced a para-substituted phenol derivative of the kind corresponding to the kinds of the phenol compound and the organic halide, as described later.

From phenol compounds of the formula(I) in which A is a hydrogen atom, para-hydroxybenzaldehydes, para-hydroxybenzoic acids or para-allyl phenols are obtained.

From phenol compounds of the formula(I) in which A is a substituent other than hydrogen, namely, a substituted or unsubstituted alkyl group, a substituted or unsubstituted allyl group, substituted or unsubstituted alkoxyl group or substituted or unsubstituted aryl group, there is obtained 4-dihalomethyl-2,5-cyclohexadienone derivatives or 4-allyl-2,5-cyclohexadienone derivatives are obtained. Specifically, when A in the formula(I) is hydrogen, there is obtained a para-substituted phenol deviative represented by the formula(II)

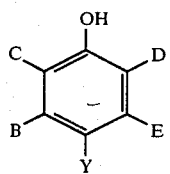

(II)

wherein B, C, D and E are as defined above and Y stands for an aldehyde group, a carboxyl group or a substituted or unsubstituted allyl group. Whereas, when A in the formula(I) is a halogen, a substituted or unsubstituted alkyl group, a substituted or unsubstituted allyl group, a substituted or unsubstituted alkoxyl group or a substituted or unsubstituted aryl group, there is obtained a para-substituted phenol derivative represented by the formula(III)

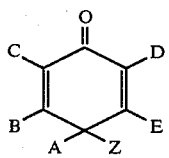

(III)

wherein A, B, C, D and E are as defined above, provided that A does not stand for a hydroxyl group, a carboxyl group or a sufonic group, and Z stands for a haloform residue or a substituted or unsubstituted allyl group.

In the process of the present invention, when said organic halide is a member selected from a haloform and a carbon tetrahalide, a hydroxychalcone compound can be obtained by, following the step(1) and before the step(2), (1a) adding to said reaction mixture the following reactant system:

(i) acetophenone or a derivative thereof,
(ii) a carbon tetrahalide and acetophenone in this order, or
(iii) a haloform and acetophenone or a derivative thereof in this order, provided that when said organic halide is a haloform, the reactant system is a system(i) or (ii), and when said organic halide is a carbon tetrahalide, the reaction system is a system(iii), thereby effecting a reaction to obtain a hydroxychalcone compound as the para-substituted phenol derivative. The reaction mixture obtained in the step(1) contains the used fixed cyclodextrin. In the step (1a), the dissolution of the above-mentioned reactant systems (i)-(iii) into the reaction system is accelerated by virtue of the presence of the used fixed cyclodextrin, leading to the acceleration of the reaction rate. As a result, a hydroxychalcone compound can be obtained in high yield in a short period of time. Where the reactant system is a system(i), there is obtained a 4-hydroxychalcone compound as the para-substituted phenol derivative. Where the reactant system is a system(ii), there is obtained a 4-hydroxy-3-carboxychalcone compound as the para-substituted phenol derivative. Where the reactant system is a system(iii), there is obtained a 2-hydroxy-5-carboxychalcone compound as the para-substituted phenol derivative. As the acetophenol derivative, there may be employed, for example, hydroxyacetophenone, methylacetophenone, nitroacetophenone, carboxyacetophenone, sulfoacetophenone, carboxyalkoxyacetophenone and sulfoalkoxyacetophenone. In the preparation of the hydroxychalcone compound, the acetophenone or its derivative may be employed in an amount of preferably 1 to 20 mols, more preferably 1 to 2 mols per mol of the phenol compound used. In this case, the molar ratio of the fixed cyclodextrin to the phenol compound is preferably 0.01 to 10, more preferably 0.1 to 5. Where the reactant system is a system(ii), the carbon tetrahalide is generally employed in an amount of 1 to 20 in terms of molar ratio relative to the phenol compound employed inthe step(1). Where the reactant system is a system(iii), the haloform is generally employed in an amount of 1 to 20 in terms of molar ratio relative to the phenol compound employed in the step(1). The reaction temperature in the step (1a) is not critical, but is generally 0° to 120° C. In practicing the process of the present invention, it is preferred that at the time of addition of the above-mentioned reactant system to the reaction system, the conversion be preferably 50 to 100% in the reaction of the reagent, which is different in kind from the reagent to be now added and which had been added previously, with the phenol compound or the intermediate derived therefrom.

In the process of the present invention, a reaction mixture containing an intended para-substituted phenol derivative is obtained by the above-mentioned reaction and, thereafter, the catalyst, i.e., the fixed cyclodextrin can easily be separated and recovered from the reaction mixture by methods such as centrifugation and filtration. The recovered solid can be used again as a catalyst repeatedly. On the other hand, the remaining reaction mixture from which the catalyst has been removed is subjected to extraction with ether. The ether layer is washed with water and then dried to obtain a para-substituted phenol derivative.

The process of the present invention may be practiced by passing an alkaline aqueous solution containing a phenol compound and an organic halide over a fixed bed of a fixed cyclodextrin, or by contacting the solution with the fixed bed. For preparing a hydroxychalcone compound, the process of the present invention may be practiced in such a manner that while passing an alkaline solution of a phenol over a fixed bed of a fixed cyclodextrin or contacting the solution with the bed, the phenol compound is reacted with a haloform and an acetophenone compound in this order, a haloform, a carbon tetrahalide and an acetophenone compound in this order, or a carbon tetrahalide, a haloform and an acetophenone in this order. In this mode of practice, there is required no operation for separation of the solid catalyst by means of centrifugation or filtration.

In practicing the process of the present invention, when a carbon tetrahalide is used as the organic halide the reaction may be effected by adding a copper catalyst to the reaction system. As the copper catalyst, there may be mentioned, for example, copper powders, copper(II) sulfate, a copper(II) halide and copper(II) oxide. In general, the copper catalyst is added in an amount of 1 to 10% by weight based on the phenol compound.

As apparent from the foregoing, according to the process of the present invention, not only the intended para-substituted phenol derivatives can be produced in high yield and with high selectivity, but also the fixed cyclodextrin employed as the catalyst can extremely easily be separated and recovered from the reaction mixture by means of, for example, centrifugation and filtration without any loss of the fixed cyclodextrin. Moreover, the recovered fixed cyclodextrin can be used repeatedly for the preparation of para-substituted phenol derivatives without lowering in yield and selectivity. Thus, the process of the present invention is extremely advantageous from the commercial standpoint.

PREFERRED EMBODIMENTS OF THE INVENTION

The present invention will be illustrated in more detail with reference to the following Examples, but should not be construed as limiting the scope of the invention. Unless otherwise specified, reactions were carried out at atmospheric pressure in Examples and Comparative Examples.

In Examples and Comparative Examples, the yield of and the selectivity for a produced para-substituted phenol derivative are respectively those obtained by the follwoing formulae:

Yield of a para-substituted phenol derivative (%) = (1)

$$\frac{\text{mole number of produced para-substituted phenol derivative}}{\text{mole number of fed phenol}} \times 100$$

Selectivity for a para-substituted phenol derivative (%) = (2)

$$\frac{\text{mole number of produced para-substituted phenol derivative}}{\left(\begin{array}{c}\text{total of mole numbers of isomers in the}\\ \text{produced substituted phenol derivatives}\end{array}\right)} \times 100$$

EXAMPLE 1

Hydroxyl groups of β-cyclodextrin are crosslinked with 2-hydroxy-n-propylene group to prepare a solid, fixed β-cyclodextrin in the manner as described below.

In 80 ml of an aqueous 50% sodium hydroxide solution is dissolved 50 g of β-cyclodextrin (special grade reagent, manufactured and sold by Nakarai Chemical Ltd., Japan). To the resulting solution is added 50 mg of sodium borohydride (special grade reagent, manufactured and sold by Yoneyama Yakuhin Kogyo Co., Ltd., Japan). 34 ml of epichlorohydrin (special grade reagent, manufactured and sold by Tokyo Kasei Co., Ltd., Japan) is dropwise added to the mixture with agitating by means of a magnetic stirrer. The resulting mixture is allowed to react at 50° C. for 40 minutes. The resulting solid is washed with acetone 3 times and with water throughly, and then dried in vacuum at 60° C. for 12 hours. Thus, there is obtained 50 g of a fixed β-cyclodextrin which is white particles having a particle diameter of 1 to 3 mm. As a result of elementary analysis of the fixed β-cyclodextrin, the carbon and hydrogen contents are found to be 47.0% and 6.6%, respectively. Therefore, the fixed β-cyclodextrin contains 87% by weight of β-cyclodextrin.

To 20 ml of an aqueous 20% of sodium hydroxide solution are added 1.5 g of the above-obtained fixed β-cyclodextrin (hereinafter often referred to as "catalyst") and 1.5 g of phenol (first class grade reagent, manufactured and sold by Kaso Chemical Co., Ltd., Japan), and further are added 3 ml of carbon tetrachloride (first class grade reagent, Tokyo Kasei Co., Ltd., Japan) and 0.1 g of copper powders (first class grade reagent, manufactured and sold by Yoneyama Yakuhin Kogyo Co., Ltd.). The reaction is allowed to proceed at 80° C. for 15 hours under reflux by the use of a reflux condenser while agitating by means of a magnetic stirrer. After completion of the reaction, the catalyst is removed by decantation (recovery of catalyst: 100%). The obtained reaction mixture is acidified with hydrochloric acid, and subjected to extractions each with 50 ml of ethyl ether 3 times. The ethyl ether layer is washed with water and then dried, thereby to obtain 2.1 g of a product. The obtained product is subjected to analysis by liquid chromatography [using a column (LS410K, MeOH-100, 30 cm) manufactured and sold by Toyo Soda Co., Ltd., Japan at 20° C., with a mixed solvent of water and ethanol (6:4)]. As a result, it is found that the product is a mixture of 2.0 g of para-hydroxybenzoic acid and 0.1 g of phenol and contains no salicylic acid. Namely, the yield of para-hydroxybenzoic acid is 91% on molar basis, and the selectivity is 100%.

After the above reaction, the above-recovered catalyst and 1.5 g of phenol are added to 20 ml of an aqueous 20% sodium solution. To the resulting mixture are added 3 ml of carbon tetrachloride and 0.1 g of copper powder. The reaction is allowed to proceed at 80° C. for 15 hours under reflux by the use of a reflux condenser while agitating by means of a magnetic stirrer. After completion of the reaction, the catalyst is removed by decantation (recovery of catalyst: 100%). The resulting solution is acidified with hydrochloric acid, and subjected to extractions each with 50 ml of ethyl ether 3 times. The ethyl ether layer is washed with water, and then dried, thereby to obtain 2.2 g of a product. The obtained product is subjected to analysis by liquid chromatography. As a result, it is found that the product is a mixture of 2.1 g of para-hydroxybenzoic acid and 0.1 g of phenol, and contains no salicylic acid. Namely, the yield of para-hydroxybenzoic acid is 95% on molar basis and the selectivity is 100%.

In the same manner as mentioned above, reactions are carried out repeatedly using the above-recovered catalyst 5 times. Despite the repeated use of the catalyst, there is observed no lowering in recovery, activity and selectivity of the catalyst.

EXAMPLE 2

Substantially the same reagents and catalyst as in Example 1 are used, except that o-cresol (special grade reagent, manufactured and sold by Tokyo Kasei Co., Ltd., Japan) is used instead of phenol.

To 20 ml of an aqueous 20% sodium hydroxide solution are added 1.5 g of the catalyst prepared in Example 1 from $\beta$-cyclodixtrin and epichlorohydrin and 1.5 g of o-cresol, and further are added 3 ml of carbon tetrachloride and 0.1 g of copper powder. The reaction is allowed to proceed at 80° C. for 15 hours under reflux by the use of a reflux condenser while agitating by means of a magnetic stirrer. After completion of the reaction, the catalyst is removed by decantation (recovery of catalyst: 100%). The resulting solution is acidified with hydrochloric acid, and subjected to extractions each with 50 ml of ethyl ether 3 times. The ether layer is washed with water, and then dried, thereby to obtain 1.9 g of a product. The obtained product is subjected to analysis by liquid chromatography [using a column (LS410K, MeOH-100, 30 cm) manufactured and sold by Toyo Soda Co., Ltd., Japan, at 25° C., with a mixed solvent of water and ethanol (6:4)]. As a result, it is found that the product is a mixture of 1.8 g of 3-methyl-4-hydroxybenzoic acid and 0.1 g of o-cresol. Namely, the yield of 3-methyl-4-hydroxybenzoic acid is 85% on molar basis, and the selectivity is 100%.

EXAMPLE 3

Substantially the same reagents and catalyst as in Example 1 are used, except that m-cresol (special grade reagent, manufactured and sold by Tokyo Kasei Co., Ltd., Japan) is used instead of phenol.

To 20 ml of an aqueous 20% sodium hydroxide solution are added 1.5 g of the catalyst as prepared in Example 1 from $\beta$-cyclodextrin and epichlorohydrin and 1.5 g of m-cresol, and further are added 3 ml of carbon tetrachloride and 0.1 g of copper powder. The reaction is allowed to proceed at 80° C. for 15 hours under reflux by the use of a reflux condenser while agitating by means of a magnetic stirrer. After completion of the reaction, the catalyst is removed by decantation (recovery of catalyst: 100%). The resulting solution is acidified with hydrochloric acid, and subjected to extractions each with 50 ml of ethyl ether 3 times. The ether layer is washed with water, and then dried, thereby to obtain 2.1 g of a product. The obtained product is subjected to analysis by liquid chromatography [using a column (LS410K, MeOH-10, 30 cm) manufactured and sold by Toyo Soda Co., Ltd., Japan, at 25° C., with a mixed solvent of water and ethanol (6:4)]. As a result, it is found that the product is a mixture of 2.0 g of 2-methyl-4-hydroxybenzoic acid and 0.1 g of m-cresol. Namely, the yield of 2-methyl-4-hydroxybenzoic acid is 95% on molar basis, and the selectivity is 100%.

EXAMPLE 4

50 g of $\beta$-cyclodextrin is dissolved in 80 ml of an aqueous 50% sodium hydroxide solution. To the resulting solution is added 50 mg of sodium borohydride. 68 ml of epichlorohydrin is dropwise added to the mixture with agitating by means of a magnetic stirrer. The resulting mixture is allowed to react at 50° C. for 40 minutes. The resulting solid is washed with acetone 3 times and with water thoroughly, and then dried in vacuum at 60° C. for 12 hours, thereby to obtain 52 g of a fixed $\beta$-cyclodextrin which is white particles having a particle diameter of 1 to 3 mm. The elementary analysis of the fixed $\beta$-cyclodextrin shows that the carbon and hydrogen contents are 48.4% and 7.1%, respectively. Therefore, the fixed $\beta$-cyclodextrin contains 78% by weight of $\beta$-cyclodextrin. The obtained fixed $\beta$-cyclodextrin is used as a catalyst for the preparation of a para-substituted phenol derivative as described hereinafter.

To 20 ml of an aqueous 20% sodium hydroxide solution are added 1.5 g of the catalyst and 1.5 g of phenol, and further are added 3 ml of carbon tetrachloride and 0.1 g of copper powder. The reaction is allowed to proceed at 80° C. for 15 hours under reflux by the use of a reflux condenser while agitating by means of a magnetic stirrer. After completion of the reaction, the catalyst is removed by decantation (recovery of catalyst: 100%). The obtained solution is acidified with a hydrochloric acid, and subjected to extractions each with 50 ml of ethyl ether 3 times. The ether layer is washed with water, and then dried, thereby to obtain 1.9 g of a product. The obtained product is subjected to analysis by liquid chromatography [using a column (LS 410K, MeOH-100, 30 cm) manufactured and sold by Toyo Soda Co., Ltd., Japan, at 25° C., with a mixed solvent of water and ethanol (6:4)]. As a result, it is found that the product is a mixture of 1.8 g of para-hydroxybenzoic acid and 0.1 g of phenol. Namely, the yield of para-hydroxybenzoic acid is 82% on molar basis, and the selectivity is 100%.

COMPARATIVE EXAMPLE 1

Substantially the same procedures as in Example 1 are repeated for preparing para-hydroxybenzoic acid, except that 1.7 g of $\beta$-cyclodextrin is used instead of 1.5 g of the fixed $\beta$-cyclodextrin. After completion of the reaction, the resulting solution is acidified with 1 ml of 36% hydrochloric acid, and subjected to filtration to separate $\beta$-cyclodextrin from the reaction solution. The separated $\beta$-cyclodextrin is dried. Thus, there is obtained 1.4 g of a recovered $\beta$-cyclodextrin (recovery: 82%). On the other hand, the filtrate is subjected to extractions each with 50 ml of ethyl ether 3 times. The ethyl ether layer is washed with water, and then dried, thereby to obtain 2.1 g of a product. The obtained product is subjected to analysis by liquid chromatography. As a result, it is found that the product is a mixture of 2.0 g of para-hydroxybenzoic acid and 0.1 g of phenol, and contains no salicylic acid. Namely, the yield of para-hydroxybenzoic acid is 92% on molar basis, and the selectivity is 100%.

The synthesis of para-hydroxybenzoic acid is carried out in substantially the same manner as in the above, except that 1.4 g of the above-recovered $\beta$-cyclodextrin is used in combination with 0.3 g of a fresh $\beta$-cyclodextrin. After completion of the reaction, the reaction mixture is acidified with a 1 ml of 35% hydrochloric acid, and subjected to filtration to separate β-cyclodextrin from the reaction mixture. The separated β-cyclodextrin is dried. Thus, there is obtained 1.3 g of a recovered β-cyclodextrin (recovery: 76%). On the other hand, the filtrate is subjected to extractions each with 50 ml of ethyl ether 3 times. The ethyl ether layer is washed with water, and then dried, thereby to obtain 2.0 g of a product. The obtained product is subjected to analysis by liquid chromatography. As a result, it is found that the product is a mixture of 1.9 g of para-hydroxybenzoic acid and 0.1 g of phenol and contains no salicylic acid. Namely, the yield of para-hydroxybenzoic acid is 90% on molar basis, and the selectivity is 100%.

In the same manner as in the above, the preparation of para-hydroxybenzoic acid is repeated 5 times using the recovered β-cyclodextrin while making up the lost β-cyclodextrin. As a result, the recovery of β-cyclodextrin is 72 to 88%, and the yield and selectivity of para-hydroxybenzoic acid are 85 to 92% on molar basis and 100%, respectively.

EXAMPLE 5

To 20 ml of an aqueous 20% sodium hydroxide solution are added 4.5 g of the catalyst (fixed β-cyclodextrin) prepared in Example 1 and 0.5 g of phenol (first class grade reagent, manufactured by Koso Chemical Co., Ltd., Japan). The resulting mixture is heated to 60° C. while agitating by means of a magnetic stirrer. Then, while dropwise adding 3 ml of chloroform (special grade reagent, manufactured and sold by Tokyo Kasei Co., Ltd., Japan) to the mixture, the reaction is allowed to proceed for 12 hours. During the course of the reaction, chloroform is added dropwise so that the molar ratio of the fixed cyclodextrin to the chloroform in the reaction system is maintained at a level of 1.0 to 1.6. The control of the molar ratio of the fixed cyclodextrin to chloroform in the reaction system is effected as follows. Every two hours during the course of the reaction, part of the reaction mixture is taken, and subjected to the determination of chloroform contained therein by means of 701-type Gas Chromatograph manufactured by Ohkura Rikagaku Kenkyusho Co., Ltd., Japan (packing material, Porapak Q manufactured and sold by Gasukuro Kogyo Inc., Japan; column length, 2 m; column temperature, 30° C.; carrier gas, helium), and the rate of addition of chloroform is adjusted. After completion of the reaction, the catalyst is removed by decantation. The recovery of the catalyst is 100%. The resulting solution is acidified with hydrochloric acid, and subjected to extractions each with 50 ml of ethyl ether 3 times. The ether layer is washed with water, and then dried, thereby to obtain 0.58 g of a product. The obtained product is subjected to analysis by means of Gas Chromatograph (Tenax GC column, 2 m, 300° C.). As a result, it is found that the product is a mixture of 0.56 g of 4-hydroxybenzaldehyde and 0.02 g of phenol, and there is detected no 2-hydroxybenzaldehyde. Namely, the yield of 4-hydroxybenzaldehyde is 86% on molar basis, and the selectivity is 100%.

Subsequently, the synthesis of 4-hydroxybenzaldehyde is carried out in substantially the same manner as in the above, except that the above-recovered catalyst is used. There is obtained 0.65 g of a product. The analysis of the product by means of Gas Chromatograph shows that the product is a mixture of 0.62 g of 4-hydroxybenzaldehyde and 0.03 g of phenol, and contains no detectable amount of 2-hydroxybenzaldehyde. Namely, the yield of 4-hydroxybenzaldehyde is 96% on molar basis, and the selectivity is 100%.

EXAMPLE 6

To 50 ml of an aqueous 20% sodium hydroxide solution are added 4.50 g of the catalyst (fixed β-cyclodextrin) as prepared in Example 1 and 0.50 g of o-cresol. The resulting mixture is heated to 60° C. while agitating by means of a magnetic stirrer. Then, while dropwise adding 3 ml of chloroform (special grade reagent, manufactured and sold by Tokyo Kasei Co., Ltd., Japan) to the mixture in the same manner as in Example 5, the reaction is allowed to proceed for 12 hours. After completion of the reaction, the catalyst is removed by decantation. The recovery of the catalyst is 100%. The obtained reaction mixture is acidified with hydrochloric acid, and subjected to extractions each with 50 ml of ethyl ether 3 times. The ether layer is washed with water, and then dried, thereby to obtain 0.65 g of a product. The analysis of the product by means of Gas Chromatograph shows that the product is a mixture of 0.61 g of 4-hydroxy-3-methylbenzaldehyde and 0.04 g of o-cresol. Namely, the yield of 4-hydroxy-3-methylbenzaldehyde is 87% on molar basis, and the selectivity is 100%.

EXAMPLE 7

To 80 ml of an aqueous 10% sodium hydroxide solution are added 2.0 g of the catalyst (fixed β-cyclodextrin) as prepared in Example 1 and 1.0 g (10.8 mmol) of phenol (first class grade reagent, manufactured and sold by Koso Chemical Co., Ltd., Japan). Then, while dropwise adding to the mixture 1.5 ml (18.7 mmol) of chloroform (special grade reagent, manufactured and sold by Tokyo Kasei Co., Ltd., Japan) in the same manner as in Example 5, the reaction is allowed to proceed at 70° C. for 10 hours while agitating by means of a magnetic stirrer. The reaction mixture is cooled thoroughly with ice, and 1.3 g (10.8 mmol) of acetophenone (special grade reagent, manufactured and sold by Tokyo Kasei Co., Ltd., Japan) is added little by little to the mixture. The reaction is allowed to proceed at room temperature for 10 hours. After completion of the reaction, the catalyst is removed by decantation. The recovery of the catalyst is 100%. The resulting solution is acidified with hydrochloric acid, and subjected to extractions each with 50 ml of ether 3 times. The ether layer is washed with water, and then dried, thereby to obtain 2.0 g of a product. The obtained product is subjected to analysis by means of 701-type Gas Chromatograph manufactured by Ohkura Rikagaku Kenkyusho Co., Ltd., Japan (packing material: Uniport HP manufactured and sold by Gasukuro Kogyo inc., Japan; column length, 2 m; column temperature, 120° C.; carrier gas, helium). As a result, it is found that the product is 4-hydroxychalcone entirely. Namely, the yield of the intended product is 84% on molar basis, and the selectivity is 100%.

EXAMPLE 8

To 80 ml of an aqueous 20% sodium hydroxide solution are added 2.0 g of the catalyst (fixed β-cyclodextrin) prepared in Example 1, 1.0 g (10.8 mmol) of phenol and 0.01 g (0.16 mmol) of copper powder (first class grade reagent, manufactured and sold by Yoneyama Yakuhin Kogyo Co., Ltd., Japan). Then, while dropwise adding 2 ml (20.0 mmol) of chloroform (special grade reagent, manufactured and sold by Tokyo Kasei Co., Ltd., Japan) to the mixture, the reaction is allowed to proceed at 60° C. for 10 hours with agitating by means of a magnetic stirrer. During the course of the reaction, the rate of addition of chloroform is controlled according to the method described in Example 5 so that the molar ratio of the fixed β-cyclodextrin (based on β-cyclodextrin) to the chloroform is maintained at a level of 1 to 2. Subsequently, while dropwise adding 2 ml (24.0 mmol) of chloroform in the same manner as in Example 5, the reaction is allowed to proceed at 60° C. for 10 hours with agitating by means of a magnetic stirrer. The reaction mixture is cooled thoroughly with ice, and 2.5 g (16.2 mmol) of 4-hydroxyacetophenone (special grade reagent, manufactured and sold by Tokyo Kasei Co., Ltd., Japan) is added little by little to the mixture. The reaction is allowed to proceed at room temperature for 10 hours. Then, the catalyst is removed by decantation. The recovery of the catalyst is 100%. The resulting solution is acidified with hydrochloric acid, and subjected to extractions each with 50 ml of ethyl ether 3 times. The ether layer is washed with water, and then dried, thereby to obtain 2.6 g of a product. The product is subjected to determinations of infrared spectrum by means of IR-E type-spectrophotometer manufactured and sold by Japan Spectroscopic Co., Ltd., Japan, and $^1$H-NMR spectrum by means of PS-100 type high resolution spectrometer manufactured and sold by Nihon Denshi Co., Ltd., Japan. The infrared spectrum and $^1$H-NMR spectrum of the product are in agreement with those of a standard sample of 2,4'-dihydroxy-5-carboxychalcone. Namely, the yield of the intended product is 86% on molar basis and the selectivity is 100%.

EXAMPLE 9

To 80 ml of an aqueous 20 % of sodium hydroxide solution are added 2.0 g of the catalyst (fixed β-cyclodextrin) prepared in Example 1, 1.0 g (10.8 mmol) of phenol and 0.01 g (0.16 mmol) of copper powder. Then, while dropwise adding to the mixture 2 ml (24.0 mmol) of chloroform in the same manner as in Example 5, the reaction is allowed to proceed at 60° C. for 10 hours with agitating by means of a magnetic stirrer. Subsequently, while dropwise adding 2 ml (20.0 mmol) of carbon tetrachloride little by little in the same manner as in Example 8, the reaction is allowed to proceed at 60° C. for 10 hours with agitating by means of a magnetic stirrer. The reaciton mixture is cooled thoroughly with ice, and 2.2 g (16.2 mmol) of 4-hydroxyacetophenone (special grade reagent, manufactured and sold by Tokyo Kasei Co., Ltd., Japan) is added little by little to the mixture. The reaction is allowed to proceed at room temperature for 10 hours. Then, the catalyst is removed by decantation. The recovery of the catalyst is 100%. The resulting solution is acidified with hydrochloric acid, and subjected to extractions each with 50 ml of ethyl ether 3 times. The ether layer is washed with water, and then dried, thereby to obtain 2.8 g of a product. The infrared spectrum and $^1$H-NMR spectrum of the product are in agreement with those of a standard sample of 4,4'-dihydroxy-3-carboxychalcone. Namely, the yield of the intended product is 92% on molar basis and the selectivity is 100%.

EXAMPLE 10

In 80 ml of an aqueous 50% sodium hydroxide solution is dissolved 50 g of α-cyclodextrin (special grade reagent, manufactured and sold by Nakarai Chemical Ltd., Japan). To the resulting solution is added 50 mg of sodium borohydride (special grade reagent, manufactured and sold by Yoneyama Yakuhin Kogyo Co., Ltd., Japan). 34 ml of epichlorohydrin (special grade reagent, manufactured and sold by Tokyo Kasei Co., Ltd., Japan) is dropwise added to the resulting mixture with agitating by means of a magnetic stirrer. Then, the reaction is allowed to react at 50° C. for 40 minutes. The resulting solid is washed with acetone 3 times and with water thoroughly, and then dried in vacuum at 60° C. for 12 hours, thereby to obtain 46 g of a fixed α-cyclodextrin which is white particles having a particle diameter of 1 to 3 mm. The elementary analysis of the fixed α-cyclodextrin shows that the carbon and hydrogen contents are 44.5% and 6.3%, respectively. Therefore, the fixed α-cyclodextrin contains 82% by weight of α-cyclodextrin.

4-Hydroxybenzaldehyde is prepared in substantially the same manner as in Example 5 except that 4.5 g of the above-obtained fixed α-cyclodextrin is used as a catalyst. The recovery of the catalyst, the yield of and the selectivity for 4-hydroxybenzaldehyde are 100%, 8% on molar basis and 95%, respectively.

Subsequently, 4-hydroxybenzaldehyde is prepared in substantially the same manner as in the above, except that the above-recovered catalyst is used. The recovery of the catalyst, the yield of and the selectivity for 4-hydroxybenzaldehyde are 100%, 65% on molar basis and 95%, respectively.

In the same manner as in the above, the syntheses of 4-hydroxybenzaldehyde are carried out repeatedly using the above-recovered catalyst 5 times. As a result, the recovery of the catalyst is 100%, and there is observed no lowering in activity and selectivity of the catalyst.

EXAMPLE 11

4-Hydroxychalcone is prepared in substantially the same manner as in Example 7, except that 4.5 g of the fixed α-cyclodextrin as prepared in Example 10 is used as a catalyst instead of the fixed β-cyclodextrin. The recovery of the catalyst, the yield of and the selectivity for 4-hydroxychalcone are 100%, 52% on molar basis and 93%, respectively. In the same manner as in the above, the syntheses of 4-hydroxychalcone are carried out repeatedly using the above-recovered catalyst 5 times. As a result, the recovery of the catalyst is 100%, and there is observed no lowering in activity and selectivity of the catalyst.

EXAMPLE 12

2,4'-Dihydroxy-5-carboxychalcone is prepared in substantially the same manner as in Example 8, except that 4.5 g of the fixed α-cyclodextrin prepared in Example 10 is used as a catalyst instead of the fixed β-cyclodextrin. The recovery of the catalyst, the yield of and the selectivity for 2,4-dihydroxy-5-carboxychalcone are 100%, 53% on molar basis and 93%, respectively.

In the same manner as in the above, the syntheses of 2,4'-dihydroxy-5-carboxychalcone are carried out repeatedly using the above-recovered catalyst 5 times. As a result, the recovery of the catalyst is 100%, and there is observed no lowering in activity and selectivity of the catalyst.

EXAMPLE 13

4.4'-Dihydroxy-3-carboxychalcone is prepared in substantially the same manner as in Example 9, except that 4.5 g of the fixed α-cyclodextrin as prepared in Example 10 is used as a catalyst instead of the fixed α-cyclodextrin. The recovery of the catalyst, the yield of and the selectivity for 4,4'-dihydroxy-3-carboxychalcone are 100%, 51% on molar basis and 92%, respectively.

In the same manner as in the above, the syntheses of 2,4'-dihydroxy-3-carboxychalcone are carried out repeatedly using the above-recovered catalyst 5 times. As a result, the recovery of the catalyst is 100%, and there is observed no lowering in activity and selectivity of the catalyst.

EXAMPLE 14

In 50 ml of an aqueous 1% sodium hydroxide solution are dissolved 8.6 g of the catalyst (fixed α-cyclodextrin) prepared in Example 10 and 0.2 g of 2,4,6-trimethylphenol (special grade reagent, manufactured and sold by Tokyo Kasei Co., Ltd., Japan). While dropwise adding 0.9 g of allyl bromide (special grade reagent, manufactured and sold by Tokyo Kasei Co., Ltd., Japan) to the mixture, the reaction is allowed to proceed at room temperature for 24 hours. During the course of the reaction, the rate of addition of allyl bromide is controlled according to the method described in Example 5 so that the molar ratio of the fixed α-cyclodextrin (based on α-cyclodextrin) to the allyl bromide is maintained at a level of 1 to 2. Subsequently, the catalyst is removed by decantation. The recovery of the catalyst is 100%. The resulting solution is acidified with hydrochloric acid, and subjected to extractions each with 50 ml of ethyl ether 5 times. The ether layer is dried, thereby to obtain 0.18 g of a product. The analysis of the product by means $^1$H-NMR shows that the product contains 53% of 2,4,6-trimethyl-4-allyl-2,5-cyclohexadienone and that the contents of 2,4,6-trimethyl-6-allyl-2,4-cyclohexadienone and 2,4,6-trimethylphenyl allyl ether are 26% and 21%, respectively. Namely, the yield of the intended product is 37%, and the selectivity is 53%.

In the same manner as in the above, the syntheses of 2,4,6-trimethyl-4-allyl-2,5-cyclohexadienone are carried out repeatedly using the above-recovered catalyst 5 times. As a result, the recovery of the catalyst is 100%, and there is observed no lowering in activity and selectivity of the catalyst.

EXAMPLE 15

All the primary hydroxyl groups of α-cyclodextrin are methoxylated by the method as described in Helv. Chim. Acta., 61, 2190 (1978).

In 80 ml of an aqueous 50% sodium hydroxide solution is dissolved 50 g of the thus modified cyclodextrin, and is added 50 mg of sodium borohydride (special grade reagent, manufactured and sold by Yoneyama Yakuhin Kogyo Co., Ltd., Japan). To the resulting solution is dropwise added 34 ml of epichlorohydrin (special grade reagent, manufactured and sold by Tokyo Kasei Co., Ltd., Japan) while agitating by means of a magnetic stirrer. The reaction is allowed to proceed at 50° C. for 40 minutes. The resulting solid is washed with acetone 3 times and with water thoroughly, and then dried in vacuum at 60° C. for 12 hours. There is obtained 42 g of a fixed modified cyclodextrin which is white particles having a particle diameter of 1 to 3 mm. The elementary analysis of the fixed modified cyclodextrin shows that the carbon and hydrogen contents are 50.9% and 7.7%, respectively. Therefore, the fixed modified cyclodextrin contains 80% by weight of the modified cyclodextrin.

2,4,6-trimethyl-4-allyl-2,5-cyclohexadienone is prepared in substantially the same manner as in Example 14 except that 8.6 g of the fixed modified cyclodextrin as prepared above is used as a catalyst instead of the fixed β-cyclodextrin. As a result, the recovery of the catalyst, the yield of and the selectivity for the intended product are 100%, 48% on molar basis and 78%, respectively.

In the same manner as in the above, the catalyst is used repeatedly 5 times. As a result, the recovery of the catalyst is 100%, and there is observed no lowering in activity and selectivity of the catalyst.

EXAMPLE 16

In 80 ml of an aqueous 50% sodium hydroxide solution is dissolved 50 g of β-cyclodextrin and is added 50 mg of sodium borohydride. 4.8 ml of epichlorohydrin is dropwise added to the solution with agitating by means of a magnetic stirrer. The reaction is allowed to proceed at 50° C. for 40 minutes. The resulting product is subjected to purification three times by the reprecipitation method using an acetone-water system, thereby to obtain a paste-like catalyst. The measurement of $^1$H-NMR of the catalyst in heavy water shows that the ratio of β-cyclodextrin residue to 2-hydroxypropyl group in the catalyst is 1.2 (β-cyclodextrin content: 94% by weight).

To 20 ml of an aqueous 20% sodium hydroxide solution are added 1.5 g of the catalyst and 1.5 g of phenol, and further are added 3 ml of carbon tetrachloride and 0.1 g of copper powder. The reaction is allowed to react at 80° C. for 15 hours under reflex by the use of a reflux condenser while agitating with a magnetic stirrer. After completion of the reaction, the resulting solution is acidified, and subjected to extractions each with 50 ml of ether 3 times. The ether layer is washed with water, and then dried, thereby to obtain 2.2 g of a product. The catalyst is separated from the water layer by centrifugation (recovery: 100%). The obtained product is subjected to analysis by liquid chromatography using a column (LS410 K, MeOH-100, 30 cm) manufactured and sold by Toyo Soda Co., Ltd., Japan, at 25° C., with a mixed solvent of water and ethanol (6:4). As a result, it is found that the product is para-hydroxybenzoic acid. Namely, the yield of para-hydroxybenzoic acid is 95% on molar basis and the selectivity is 100%.

EXAMPLE 17

In 80 ml of an aqueous 20% sodium hydroxide solution is dissolved 50 g of β-cyclodextrin (special grade reagent, manufactured and sold by Nakarai Chemical Ltd., Japan), and is added 50 ml of sodium borohydride (special grade reagent, manufactured and sold by Yoneyama Yakuhin Kogyo Co., Ltd., Japan). 50 ml of ethylene glycol glicydyl ether (first class grade reagent, manufactured and sold by Tokyo Kasei Co., Ltd., Japan) is dropwise added to the solution with agitating by means of a magnetic stirrer. The reaction is allowed to proceed at 50° C. for 40 minutes. The produced solid is washed with acetone 3 times and with water thoroughly, and then dried in vacuum at 60° C. for 12 hours. There is obtained 44 g of a fixed β-cyclodextrin which is white particles having a diameter of 1 to 3 mm. The elementary analysis of the fixed β-cyclodextrin shows that the carbon and hydrogen contents are 52.8% and 8.1%, respectively. Therefore, the fixed β-cyclodextrin contains 60% by weight of β-cyclodextrin.

To 20 ml of an aqueous 20% sodium hydroxide solution are added 1.5 g of the above-obtained fixed β-cyclodextrin and 1.5 g of phenol (first class grade reagent, manufactured and sold by Koso Chemical Co., Ltd., Japan), and further are added 3 ml of carbon tetrachloride (first class grade reagent, manufactured and sold by Tokyo Kasei Co., Ltd., Japan) and 0.1 g of copper powder (first class grade reagent, manufactured and sold by Yoneyama Yakuhin Kogyo Co., Ltd., Japan). The reaction is allowed to proceed at 80° C. for 15 hours under reflux by the use of a reflux condenser while agitating by means of a magnetic stirrer. After completion of the reaction, the catalyst is removed by decantation (recovery of catalyst: 100%). The resulting solution is acidified with hydrochloric acid, and subjected to extractions each with 50 ml of ethyl ether 3 times. The ether layer is washed with water, and then dried, thereby to obtain 2.0 g of a product. The obtained product is subjected to analysis by liquid chromatography [using a column (LS410 K, MeOH-100, 30 cm) manufactured and sold by Toyo Soda Co., Ltd., at 25° C., with a mixed solvent of water and ethanol (6:4)]. As a result, it is found that the product is a mixture of 1.9 g of para-hydroxybenzoic acid and 0.1 g of phenol and contains no salicylic acid. Namely, the yield of para-hydroxybenzoic acid is 86% on molar basis and the selectivity is 100%.

Subsequently, the above-recovered catalyst and 1.5 g of phenol were added to 20 ml of an aqueous 20% sodium hydroxide solution. To the resulting mixture are added 3 ml of carbon tetrachloride and 0.1 g of copper powder. The reaction is allowed to proceed at 80° C. for 15 hours under reflux by the use of a reflux condenser while agitating by means of a magnetic stirrer. After completion of the reaction, the catalyst is removed by decantation (recovery of catalyst: 100%). The resulting solution is acidified with hydrochloric acid, and subjected to extractions each with 50 ml of ethyl ether 3 times. The ether layer is washed with water, and then dried, thereby to obtain 2.2 g of a product. The product is subjected to analysis by liquid chromatography. As a result, it is found that the product is a mixture of 2.1 g of para-hydroxybenzoic acid and 0.1 g of phenol and contains no salicylic acid. Namely, the yield of and the selectivity for para-hydroxybenzoic acid are 95% on molar basis and 100%, respectively.

In the same manner as in the above, the catalyst is used repeatedly 5 times. As a result, there is observed no lowering in recovery, activity and selectivity of the catalyst.

PROBABILITY OF UTILIZATION IN INDUSTRY

According to the process of the present invention, not only a variety of useful para-substituted phenol derivatives can be prepared from phenol compounds in high yield and with high selectivity, but also the fixed cyclodextrin employed as the catalyst can extremely easily be recovered from the reaction mixture by means of, e.g., centrifugation and filtration without any loss of the fixed cyclodextrin. Moreover, the recovered fixed cyclodextrin can be used repeatedly as a catalyst in the process of the present invention without lowering in yield of and selectivity for para-substituted phenol derivatives, thus enabling the commercially advantageous production process of the desired products to be realized.

What is claimed is:

1. A process for producing a para-substituted phenol derivative which comprises:
   (1) reacting a phenol compound represented by the formula (I)

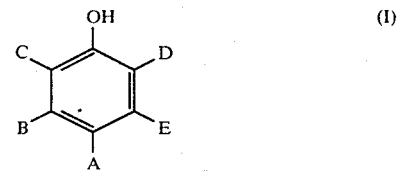

wherein A, B, C, D and E each independently stand for hydrogen, a hydroxyl group, a carboxyl group, a sulfonic group, a halogen atom a substituted or unsubstituted alkyl group, a substituted or unsubstituted alkoxyl group or a substituted or unsubstituted aryl group, provided that A does not stand for a hydroxyl group, a carboxyl group and a sulfonic group and that when two or more of A, B, C, D, and E each independently stand for a substituted or unsubstituted alkyl group or a substituted or unsubstituted alkoxyl group, they have their respective free terminal ends or at least one of them is bonded to another group selected from said alkyl and alkoxyl groups to form a ring, with an organic halide selected from the group consisting of a haloform, a carbon tetrahalide and a substituted or unsubstituted allyl halide in the presence of an alkali metal hydroxide, using as a catalyst a fixed cyclodextrin having hydroxyl groups crosslinked with a bivalent hydrocarbon group having free valences at its both ends, said hydrocarbon group having at least one hydrogen atom substituted or unsubstituted with a member selected from the group consisting of an alkyl group, a halogen atom and a hydroxyl group and containing or not containing at least one combination of two neighboring carbon atoms having therebetween at least one member selected from the group consisting of an oxygen atom, a sulfur atom and phenylene, thereby to obtain a reaction mixture containing a para-substituted phenol derivative; and
   (2) isolating the para-substituted phenol derivative from said reaction mixture.

2. A process according to claim 1, wherein said hydrocarbon group has carbon atoms of 2 to 20.

3. A process according to claim 2, wherein said hydrocarbon group is represented by the following formulae (IV) to (VII):

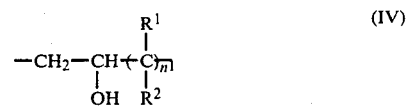

wherein $n^1$ is an integer from 1 to 10, and $R^1$ and $R^2$ each independently stand for a hydrogen atom, a halogen atom, a hydroxyl group or an alkyl group having 6 or less carbon atoms;

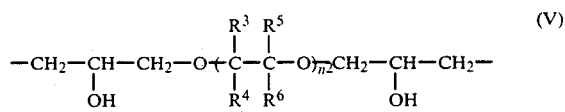

wherein $n^2$ is an integer from 1 to 6, and $R^3$, $R^4$, $R^5$, and $R^6$ each independently stand for a hydrogen atom, a halogen atom, a hydroxyl group or an alkyl group having 6 or less carbon atoms;

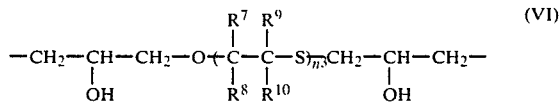

wherein $n^3$ is an integer from 1 to 6, and $R^7$, $R^8$, $R^9$ and $R^{10}$ each independently stand for a hydrogen atom, a halogen atom, a hydroxyl group or an alkyl group having 6 or less carbon atoms; and

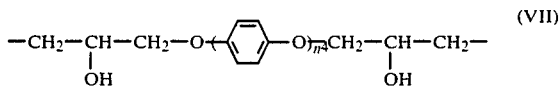

wherein $n^4$ is an integer from 1 to 2.

4. A process according to claim 3, wherein said hydrocarbon group is a member selected from the group consisting of 2-hydroxypropylene and 2,9-dihydroxy-4,7-dioxadecylene.

5. A process according to claim 1, wherein said cyclodextrin is a member selected from the group consisting of α-cyclodextrin, β-cyclodextrin and γ-cyclodextrin.

6. A process according to claim 5, wherein said cyclodextrin is α-cyclodextrin.

7. A process according to claim 6, wherein said organic halide is an allyl halide.

8. A process according to claim 5, wherein said cyclodextrin is β-cyclodextrin.

9. A process according to claim 8, wherein said organic halide is a member selected from the group consisting of a haloform and a carbon tetrahalide.

10. A process according to claim 1, wherein said substituted or unsubstituted alkyl group, said substituted or unsubstituted allyl group, said substituted or unsubstituted alkoxyl group and said substituted or unsubstituted aryl group each have carbon atoms of not more than 6 with respect to B, C, D and E and each have carbon atoms of not more than 12 with respect to A.

11. A process according to claim 1, wherein said alkali metal hydroxide is sodium hydroxide or potassium hydroxide.

12. A process according to claim 1, wherein said fixed cyclodextrin is employed in an amount of 0.001 to 20 in terms of molar ratio of the cyclodextrin in said fixed cyclodextrin relative to said organic halide.

13. A process according to claim 1, wherein said alkali metal hydroxide is employed in an amount of 1 to 15 times the stoichiometrical amount of said alkali metal hydroxide relative to said phenol compound.

14. A process according to claim 1, wherein said organic halide is employed in an amount of 1 to 20 in terms of molar ratio relative to said phenol compound.

15. A process according to claim 1, wherein the reaction of the step(1) is effected by intermittently or gradually adding the organic halide to a system comprising the phenol compound, the alkali metal hydroxide and the fixed cyclodextrin.

16. A process according to claim 1, wherein the reaction of the step(1) is effected at 0° to 120° C.

17. A process according to claim 1, wherein the reaction of the step(1) is effected in an aqueous medium.

18. A process according to claim 1, wherein A in the formula(I) is hydrogen and said para-substituted phenol derivative is represented by the formula(II)

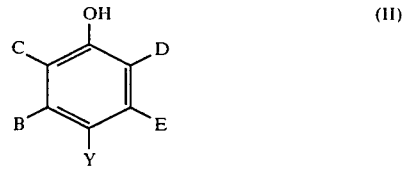

wherein B, C, D and E are as defined above and Y stands for an aldehyde group, or A in the formula(I) is a halogen atom, a substituted or unsubstituted alkyl group, a substituted or unsubstituted allyl group, a substituted or unsubstituted alkoxyl group or a substituted or unsubstituted aryl group and said para-substituted phenol derivative is represented by the formula(III)

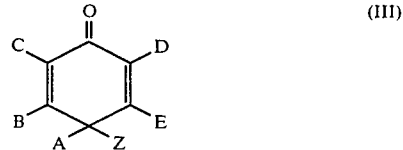

wherein A, B, C, D and E are as defined above, provided that A does not stand for a hydroxyl group, carboxyl group and sulfonic group, and Z stands for a haloform residue or a substituted or unsubstituted allyl group.

19. A process for producing a hydroxychalcone compound in accordance with claim 1, wherein said organic halide is a member selected from a haloform and a carbon tetrahalide, and which comprises, following the step(1) and before the step(2), (1a) adding to said reaction mixture the following reactant system:
(i) acetophenone or a derivative thereof,
(ii) a carbon tetrahalide and acetophenone or a derivative thereof in this order, or
(iii) a haloform and acetophenone or a derivative thereof in this order, provided that when said organic halide is a haloform, the reactant system is a system(i) or (ii), and when said organic halide is a carbon tetrahalide, the reaction system is a system(iii), thereby effecting a reaction to obtain a reaction mixture containing a hydroxychalcone compound as the para-substituted phenol derivative.

20. A process according to claim 19, wherein said reactant system is a system(i) and said hydroxychalcone compound is a 4-hydroxychalcone compound.

21. A process according to claim 19, wherein said reactant system is a system(ii) and said hydroxychalcone compound is a 4-hydroxy-3-carboxychalcone compound.

22. A process according to claim 19, wherein said reactant system is a system(iii) and said hydroxychalcone compound is a 2-hydroxy-5-carboxychalcone compound.

23. A process according to claim 19, wherein said acetophenone or its derivative is employed in an amount of 1 to 20 in terms of molar ratio relative to said phenol compound employed in the step(1).

24. A process according to claim 19, wherein said reactant system is a system(ii) and said carbon tetrahalide is employed in an amount of 1 to 20 in terms of molar ratio relative to said phenol compound employed in the step(1).

25. A process according to claim 19, wherein said reactant system is a system(iii) and said haloform is employed in an amount of 1 to 20 in terms of molar ratio relative to said phenol compound employed in the step(1).

26. A process according to claim 19, wherein the reaction of the step (1a) is effected at 0° to 120° C.

* * * * *

UNITED STATES PATENT AND TRADEMARK OFFICE
CERTIFICATE OF CORRECTION

PATENT NO. : 4,663,478

DATED : May 5, 1987

INVENTOR(S) : Hidefuni Hirai, et al.

It is certified that error appears in the above-identified patent and that said Letters Patent is hereby corrected as shown below:

| | |
|---|---|
| Col. 3, lines 3-4 | Delete "deposite" and substitute --deposit-- |
| Col. 3, line 26 | Correct spelling of --hydroxybenzaldehyde-- |
| Col. 4, line 8 | After "comprises" delete "(1)" |
| Col. 4, line 29 | Correct spelling of --group-- |
| Col. 9, line 32 | Correct spelling of --derivative-- |
| Col. 9, line 62 | Delete "sufonic" and substitute --sulfonic-- |
| Col. 10, line 43 | Insert space between "in" and "the" |
| Col. 11, line 53 | Correct spelling of --following-- |
| Col. 14, line 54 | Delete "extrations" and substitute --extractions-- |
| Col. 17, line 47 | Correct spelling of --reaction-- |
| Col. 18, line 21 | Delete "8%" and substitute --58%-- |
| Col. 19, line 34 | After "means" insert --of-- |
| Col. 20, line 28 | Delete "1.2" and substitute --1:1.2-- |
| Col. 22, line 16 | After "atom" insert --,-- |
| Col. 23, line 1 | Delete "Rhu 5" and substitute --$R^5$-- |

Signed and Sealed this

Twenty-ninth Day of August, 1989

Attest:

DONALD J. QUIGG

Attesting Officer

Commissioner of Patents and Trademarks